United States Patent [19]

Manning

[11] 4,334,118

[45] Jun. 8, 1982

[54] SOLID PHOSPHORIC ACID CATALYZED OLEFIN POLYMERIZATION PROCESS

[75] Inventor: John F. Manning, Moraga, Calif.

[73] Assignee: Chevron Research, San Francisco, Calif.

[21] Appl. No.: 268,943

[22] Filed: Jun. 1, 1981

[51] Int. Cl.$^3$ .............................................. C07C 2/04
[52] U.S. Cl. ................................... 585/529; 585/514; 252/435; 252/437
[58] Field of Search ................. 585/529, 514; 252/435, 252/437

[56] References Cited

U.S. PATENT DOCUMENTS

| 1,993,513 | 3/1935 | Ipatieff. | |
|---|---|---|---|
| 2,596,497 | 5/1952 | Mavity. | |
| 2,909,580 | 10/1959 | Layng. | |
| 3,050,472 | 8/1962 | Morrell. | |
| 3,050,473 | 8/1962 | Morrell. | |
| 3,132,109 | 8/1964 | Young. | |
| 3,402,130 | 9/1968 | Nixon. | |
| 4,062,801 | 12/1977 | Burton et al. | 585/529 |

FOREIGN PATENT DOCUMENTS

| 241523 | 11/1962 | Australia | 585/514 |
|---|---|---|---|
| 572249 | 3/1959 | Canada | 585/514 |
| 740952 | 8/1966 | Canada | 585/514 |
| 933235 | 8/1963 | United Kingdom | 585/514 |
| 1045210 | 10/1966 | United Kingdom | 585/514 |

OTHER PUBLICATIONS

United Catalyst Incorporated, Bulletin C 84-0578, Louisville, Ky.

Primary Examiner—Thomas A. Waltz
Assistant Examiner—Asok Pal
Attorney, Agent, or Firm—J. A. Buchanan, Jr.; T. G. DeJonghe; L. S. Squires

[57] ABSTRACT

Improved processes for polymerizing $C_3$–$C_{12}$ olefins (e.g. propylene) comprising polymerizing olefins in the presence of a solid phosphoric acid catalyst and an alkanol. As well as catalyzing the polymerization, the catalyst also catalyzes the decomposition of the alkanol into water and olefin. The water in turn replaces water lost from the catalyst during the polymerization thus maintaining a more constant phosphoric acid strength catalyst without subjecting said catalyst to excess liquid water and substantially improving overall polymerization conversions and catalyst life.

9 Claims, No Drawings

SOLID PHOSPHORIC ACID CATALYZED OLEFIN POLYMERIZATION PROCESS

BACKGROUND OF THE INVENTION

1. The Invention

This invention relates to solid phosphoric acid catalyzed processes for polymerizing olefins (e.g. propylene). In a further aspect, the invention relates to a method of controlling the phosphoric acid strength of the catalyst in such processes to improve yields and catalyst life and reduce catalyst coking.

2. The Prior Art

The polymerization of olefins by contacting a mixed liquid/vapor stream of olefins with a solid phosphoric acid catalyst under polymerization conditions is well known and is, for example, disclosed in U.S. Pat. Nos. 2,596,497 and 2,909,580. The use of solid phosphoric acid catalysts was disclosed as early as 1935 in U.S. Pat. No. 1,993,513.

A major problem associated with this process is that water is removed from the solid catalyst as the process proceeds thereby increasing the phosphoric acid strength of the catalyst. This imposes a limitation on the useful life of the catalyst because the activity and selectivity of the catalyst is dependent upon exact control of the phosphoric acid strength. As the phosphoric acid strength exceeds about 104%, the formation of coke or tar is catalyzed thus substantially reducing yields and eventually requiring replacement of the catalyst as it becomes "coked-up".

This problem is recognized by the art and various solutions have been proposed. Two related solutions have been to supply water vapor along with the liquid olefin feed stream and/or to increase the amount of water in the catalyst. Both of these solutions have limitations which prevent them from replenishing any more than a portion of the water removed in the process. First, because of vapor-liquid equilibrium, insufficient water can be supplied in the vapor phase to replace the water removed during the reaction process. Moreover, water cannot be added in the liquid phase because it will severely weaken the catalyst support causing deterioration of at least a portion of the support into fine particles which in turn cause increased pressure drops through the bed and prematurely force catalyst change-out. Increasing the water in the catalyst is self-limiting and further limited by the fact the solid catalyst will deteriorate if too much water is used. It should be noted here that solid phosphoric acid catalysts are supported on Kieselguhr, or other similar materials which are very much less structurally stable than the impregnated or promoted refractory base catalysts used in other types of catalysts. Refractory base supports are generally quite stable to moisture, whereas the solid phosphoric acid catalyst supports soften and crumble into a sludge when excess moisture enters reaction. This requires premature process shutdown and increased maintenance.

A further approach described in U.S. Pat. No. 2,909,580 is the use of a solid thin film phosphoric acid catalyst with intermediate water washing steps. This approach is described as increasing the overall life of the catalyst but requires process shutdowns to perform the required water washing treatments.

SUMMARY OF THE INVENTION

The present process provides an improved solid phosphoric acid catalyzed process for polymerizing olefins. The present process provides increased catalyst life, increased long term yields, and increased operating time between catalyst replacement.

The improved process of the present invention comprises contacting a vaporized olefin feed containing a minor amount of an alkanol, with a solid phosphoric acid catalyst under polymerization conditions.

The phosphoric acid catalyst, as well as catalyzing the polymerization, will also catalyze the decomposition of the alkanol into the corresponding alkene and water. Thus, supplying the amount of water needed to maintain satisfactory hydration in the solid phosphoric acid catalyst without causing the problems associated with the prior art solutions. This is because an equilibrium results at the catalyst, wherein the water lost by the catalyst is simultaneously replenished without significant liquid build-up.

The invention will be further described hereinbelow.

FURTHER DESCRIPTION OF THE INVENTION AND PREFERRED EMBODIMENTS

The present process can be applied to the catalytic polymerization of olefins using a solid phosphoric acid catalyst and can generally be conducted in the same manner as the prior art processes with the exception of the use of a feed stream containing a minor amount of alkanol.

Suitable olefins which can be used in the present process include, for example, olefins containing from 3 through 12 carbon atoms such as, for example, propene, butene, isobutene, heptene and the like, and mixtures thereof. Frequently, the feed is a mixture of two or more of such olefins and can also contain substantial amounts of other compounds such as ethylene and recycled oligomers recovered from the reaction product.

The products of this polymerization typically have about from 2 through 6 monomer units and are useful for a variety of products and intermediates. For example polymers having 2–3 monomer units are useful for gasoline; those having 3–5 monomer units are intermediates for alkylaromatics blend stocks; those having 4–6 monomer units are useful to blend diesel fuels; those having 4–6 monomer units are useful for synthetic alkylates; and those having 5–6 monomer units are useful as modifiers in polybutene formulations and lubricants. The present process is especially applicable to the production of polymers useful for benzene alkylation in which the alkylbenzene is used as an intermediate for the preparation of surfactants.

The solid phosphoric acid catalysts used in the present process contain an acid of phosphorus such as, for example, ortho-, pyro-, or tetraphosphoric acid or mixtures thereof (for example $H_3PO_4 \cdot P_2O_5 \cdot (H_2O)_x$ which is a mixture of ortho and pyrophosphoric acid) as the principal catalytically active component on a siliceous solid carrier. Such catalysts are available commercially and are generally prepared by mixing the phosphoric acid component with a siliceous solid carrier to form a wet paste. This paste can be calcined and then crushed to yield catalyst particles, or the paste can be extruded or pelleted prior to calcining to produce more uniform catalyst particles. The support or carrier is preferably a naturally occurring porous silica-containing material such as, for example, Kieselguhr, kaolin, infusorial earth, diatomaceous earth or the like. A minor amount of various additives, such as mineral talc, fullers earth and iron compounds including iron oxide can be added to the support to increase its strength and hardness. Where additives are used, they are generally considered as part of the support, and typically comprise about from 3–20% of the total support. The relative ratio of the support, including any additives, and phosphoric acid in the catalyst can vary widely. For example, the support can comprise 10 to 95 weight percent of the catalyst but more usually comprises about 15–30% of the catalyst. The remainder of the catalyst is normally phosphoric acid (including any water contained therein).

Solid phosphoric acid catalysts are well known to the art and further details as to their composition and production can be obtained from the art such as, for example, U.S. Pat. Nos. 3,050,472; 3,050,473; 3,132,109 and 3,402,130.

The solid phosphoric acid catalyst is also defined in terms of the degree of hydration or more generally its acid strength. In accordance with conventional practice, phosphoric acid strength is calculated on the basis of its $H_3PO_4$ weight content. Thus, $H_3PO_4$ has a phosphoric acid strength of 100% whereas $H_4P_2O_7$ has a phosphoric acid strength of 110% calculated as follows:

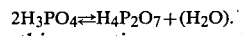

By this equation one mole of $H_4P_2O_7$ ($M_w = 178$) is equivalent to two moles of $H_3PO_4$ $M_2 = 98$. Thus, phosphoric acid strength $= [2(98) \div 1(178)] \times 100 = 110\%$.

Generally, in the present process the phosphoric acid component of the catalyst will have a phosphoric acid strength of about 100 to 108 wt. %, $H_3PO_4$ preferably about from 101 to 105 wt. % $H_3PO_4$. Best results are obtained in the practice of the present invention using catalysts having a phosphoric acid strengths of about from 102–103 wt. % $H_3PO_4$. If phosphoric acid strengths above 108% are used, substantial quantities of tars and coke are formed and catalyst life decreases. Also, as before noted, even at levels above about 104% the rate of coke formation increases. If acid concentrations below 100% $H_3PO_4$ are used, much lower conversions result and the crush strength of the catalyst is lower due to the higher water content.

The alkanols used in the present process are alkanols which are reactive under the polymerization conditions to decompose in high yields, i.e. at least 50% and preferably at least about 90%, upon contact with solid phosphoric acid catalysts, under the olefin polymerization process conditions, yielding water and alkene. Preferably, the alkanols used in the present process are secondary or tertiary alkanols and preferably have from 3 through 12 carbon atoms. Suitable alkanols thus include, for example, isopropanol, t-butanol, 2-pentanol, 4-heptanol, 2-ethyl-2-pentanol, 1,1-dimethyl-1-decanol and the like, and mixtures thereof. It is preferred to use alkanols having the same number of carbon atoms as the olefinic feed stream since the olefin degradation product will also be polymerized. For example, where propylene is being polymerized, it is preferred to use isopropanol. Thus, the degradation product will be propene which will in turn be polymerized along with the propene feedstock. The use of isopropanol is especially preferred because it decomposes upon contact with the solid phosphoric acid catalyst under the polymerization conditions in virtually 100% yields.

The polymerization process can be conducted by contacting the feed stream, containing olefin, alkanol and optionally other compatible materials, in a mixed liquid-vapor state with the solid phosphoric acid catalyst under reaction conditions. Typically the polymerization is conducted at temperatures in the range of about from 160° to 235° C. preferably about from 195° to 220° C. and pressures in the range of about from 100 psig to 1000 psig preferably about from 370 psig to 700 psig. Typically, a catalyst:olefin contact time or liquid hourly space velocity (since the process is generally conducted as continuous process) of about from 1 lit/hr. to 5 lit/hr of total olefin feed (including the alkanol additive but exclusive of any quench which may be used) per kg of catalyst; preferably about from 2.0 lit/hr to 4.5 lit/hr per kg of catalyst is used.

Because of the heat of reaction generated by the polymerization an inert quench stream is typically added to the feed stream absorbing this heat. Propane or recycled unreacted feed can be conveniently used for this purpose. Where it is desired to use a quench, the amount of quench used can be calculated on the basis of heat of reaction and the heat capacity and heat of vaporization of the quench. As above noted, feed space velocities are given exclusive of the quench.

Typically, in accordance with the practice of the present invention the olefin feed stream contains about from 0.1 mole percent to 0.5 mole percent of said alkanol, preferably about from 0.25 mole percent to 0.3 mole percent. Ideally, the amount of said alkanol is sufficient to generate sufficient water to replace the net water loss of the catalyst in the reaction system, thereby maintaining the hydration (or $H_3PO_4$ strength) of the catalyst substantially constant at the desired strength. As before mentioned, the partial pressure of water in the system at reaction conditions is such that more water exits the reactor than can be supplied in the vapor form or dissolved in the feed to the reactor.

As a first approximation, the optimum amount of alkanol can be calculated by determining the amount of water needed to replace the net catalyst water loss (i.e. water evaporated from catalyst during reaction per unit of olefin feed or time less water contained in the olefin feed e.g. water dissolved in the initial feed prior to evaporation) and then converting this to moles of said alkanol required on the basis that one mole of alkanol generates one mole of water upon decomposition at the catalyst site. The initial determination of the amount of water needed can be made on the basis of vapor pressures, reaction temperatures etc. and is a routine calculation generally used in the art. A detailed procedure for making this calculation is, for example, described in Bulletin C84-0578 of United Catalyst Incorporated of Louisville, Ky., which procedure is hereby incorporated by reference.

Optimum reaction temperatures, times, space velocities and alkanol amounts may vary with the particular olefin feed stream but can be determined by routine experimentation.

A further understanding of the invention can be had from the following non-limiting examples.

EXAMPLE 1

This example illustrates the process of the invention.

In this example 48.3 grams per minute of a mixed olefinic feed (excluding alkanol) having the composition indicated in Table A hereinbelow were preheated and then fed as a liquid-vapor mixture to a fixed bed column reactor system having four reactors operating in series. Each reactor was operated at an inlet temperature of 390° F. (i.e. 200° C.) and pressure of 390 psig (i.e. 27.4 kg/cm$^2$). Each column contained a fixed bed of commercial solid phosphoric acid catalyst initially having a phosporic acid strength of 102–103 wt. % H$_3$PO$_4$ and supported on a siliceous carrier. An overall catalyst space velocity of 1.45 grm feed/grm catalyst hr. (based on the sum total of the catalyst contained in all four columns) was used. Initially 6.85 milligrams of isopropanol per gram of C$_3$ olefin feed was injected into the olefin feed stream prior to preheating. This was sufficient, upon decomposition to provide about an additional 400 ppm (by wt.) of water in the feed stream. It was found that this amount of water caused overhydration resulting in some catalyst softening. The amount of isopropanol was then reduced to 4.28 m.g./g of C$_3$ feed. This was sufficient upon decomposition to provide about an additional 250 ppm (wt.) of water in the reaction stream. Because of the initial overhydration, some of the catalyst support screens plugged and after 1115 run hours, the bottom two inches of catalyst were removed from the catalyst bed (catalyst bed height was 4'8") in the second reactor and, replaced with fresh catalyst and after 1242 run hours the bottom two inches of catalyst in the first reactor were similarly replaced.

The reaction product from the last reactor column was then fed to a first distillation column, operating at a pressure of 190 psig and a bottom temperature of 440° F., of a two-column distillation train. The bottoms from the first column were fed to the second column and the overheads were vented to flare. The second column was operated at a pressure of 10 psig and a bottom temperature of 400° F. The bottoms were taken off as the topped polymer product and the overhead was recycled and mixed with fresh feed between the preheater and reactor.

This experiment was continued for a total of 2600 run hours (the reactors were not run continuously and results would probably have been even better because of start-up inefficiencies in bringing the system to equilibrium) and then terminated even though the system was still operating satisfactorily. The average conversion, based on topped polymer, during the run was 89%. Sixty-nine gallons of topped polymer were produced per pound of catalyst. (Topped polymer refers to the polymerization product remaining after removal (e.g. distillation) of olefins containing less than 10 carbon atoms.)

The catalyst was examined and found to have a coke content of 4.5 wt. % in the first reactor and an average coke content of 1.5 wt. % in the last three reactors. The higher coke content in the first reactor was probably caused by a greater percentage of the polymerization occurring in the first reactor which gave the largest exothermic temperature rise of the four catalyst reactors and correspondingly causing more coking in the first reactor.

The results of this example indicate a very substantial improvement over the prior art processes.

TABLE A

| Reactor Feed Composition | | | |
|---|---|---|---|
| | g | Moles | Mole % |
| C$_2$ = (ethylene) | 0.04 | 0.001 | 0.25 |
| C$_2$ = (ethane) | 0.27 | 0.009 | 1.57 |
| C$_3$ = (propylene) | 8.00 | 0.190 | 33.18 |
| C$_3$ = (propane) | 1.91 | 0.043 | 7.56 |
| C$_4$ = (butylene) | 0.21 | 0.038 | 0.65 |
| C$_4$/C$_5$ = (butane/pentane) | 0.77 | 0.013 | 2.17 |

TABLE A-continued

| Reactor Feed Composition | | | |
|---|---|---|---|
| | g | Moles | Mole % |
| LIGHT POLYMER* | 37.10 | 0.313 | 54.62 |
| | | | 100.00 |

*recycle overheads from product distillation column, consist of olefins containing less than ten carbon atoms.

EXAMPLE 2

For purposes of comparison a control run was conducted using the same feed, feed rate, reaction conditions, reactor system and catalyst as in Example 1 but without using isopropanol.

The run was stopped after 1625 hours because of the poor conversions which were then being observed. The average conversion of propylene during this run was 69% conversion of propylene to topped polymer. The yield of topped polymer per pound of catalyst was 28 gallons. The catalyst was also examined at this time for coke and found to contain 16 wt. % coke in the first reactor, 11.4 wt. % in the second reactor, 9.7 wt. % in the third reactor and 10.8 wt. % in the fourth.

By comparing the results obtained in this Example with those obtained in Example 1, it can be seen that Applicant's process increased average conversion by 27% and increased topped polymer production per pound of catalyst by 146%. Applicant's process further reduced catalyst coking by at least 70% even though the polymerization run was conducted for a substantially longer time.

Obviously many modifications and variations of the invention, described hereinabove and below in the claims, can be made without departing from the essence and scope thereof.

What is claimed is:

1. In a process for polymerizing C$_3$–C$_{12}$ olefins to produce lower polyolefins which comprises contacting a mixed liquid/vapor olefin feed stream with a solid phosphoric acid catalyst having a siliceous support under polymerization conditions, the improvement wherein said catalyst has a phosporic acid strength in the range of about from 100 to 108 wt. %, and said olefin feed stream comprises an amount of an alkanol, selected from the group consisting of alkanols which are reactive at the polymerization conditions used for said process to decompose at yields of at least 50% upon contact with said solid phosphoric acid catalyst under said polymerization conditions generating water as a decomposition product, effective to maintain the phosphoric acid strength of said catalyst within said range by replacing at least a portion of the water discharged from said catalyst during said polymerization with water generated by decomposition of said alkanol.

2. The process of claim 1 wherein said catalyst has a phosphoric acid strength of about from 101 to 105 wt. %.

3. The process of claim 1 wherein said catalyst has a phosphoric acid strength of about from 102 to 103 wt. %.

4. The process of claim 1 wherein said olefin feed stream contains about from 0.1 to 0.5 mole percent of said alkanol.

5. The process of claim 1 wherein said olefin contains about from 0.25 to 0.3 mole percent of said alkanol.

6. The process of claim 1 wherein said alkanol is a secondary or tertiary alkanol and has the same number of carbon atoms as an olefin present in substantial amounts in said feed stream.

7. The process of claims 3 or 6 wherein said feed stream comprises a substantial amount of propylene and said alkanol is isopropanol.

8. The process of claim 6 wherein said catalyst has a phosphoric acid strength of about 102–103 wt. % and said polymerization is conducted at temperatures in the range of about from 160° to 235° C. and pressures in the range of from about 100 to 1000 psig using a feed stream comprising from about 0.1 to 0.5 mole percent of said alkanol.

9. The process of claim 3 wherein said alkanol is selected from the group consisting of secondary and tertiary alkanol having 3 through 12 carbon atoms and mixtures thereof.

* * * * *